United States Patent

Yamamoto et al.

[11] Patent Number: 5,141,303
[45] Date of Patent: Aug. 25, 1992

[54] METHOD AND APPARATUS FOR DISCRIMINATING EYE FUNDUS BLOOD VESSELS

[75] Inventors: Tetsuya Yamamoto, Ibaraki; Koji Ogino; Toshiaki Sugita, both of Hino, all of Japan

[73] Assignee: Kowa Company Ltd., Japan

[21] Appl. No.: 519,875

[22] Filed: May 7, 1990

[30] Foreign Application Priority Data

May 8, 1989 [JP] Japan .................. 1-113664

[51] Int. Cl.$^5$ .......................... A61B 3/10; A61B 5/02
[52] U.S. Cl. .................. 351/211; 351/221; 128/666
[58] Field of Search ............... 351/205, 206, 221, 246; 128/633, 745, 691, 664, 665, 666; 606/4

[56] References Cited

U.S. PATENT DOCUMENTS

| 4,157,708 | 6/1979 | Imura | 128/666 |
| 4,854,692 | 8/1989 | Kobayashi | 351/221 |

Primary Examiner—Rodney B. Bovernick
Attorney, Agent, or Firm—Bruce L. Adams; Van C. Wilks

[57] ABSTRACT

Light beams of predetermined different wavelengths are projected into an eye fundus and light scattered therefrom is detected to distinguish blood vessels from surrounding tissue in the eye fundus. The method and apparatus of the invention makes full use of differences in light absorbing/reflecting characteristics in the fundus blood vessels and surrounding tissue and is therefore able to reliably distinguish whether light projected at the eye fundus is scattered by a blood vessel or by surrounding tissue.

14 Claims, 3 Drawing Sheets

METHOD AND APPARATUS FOR DISCRIMINATING EYE FUNDUS BLOOD VESSELS

BACKGROUND OF THE INVENTION

1. Field of the Invention

The present invention relates to a method and apparatus for discriminating eye fundus blood vessels, and more particularly to a method and apparatus for discriminating eye fundus blood vessels in which a light beam of prescribed wavelength is projected into the eye fundus and light scattered therefrom is detected to distinguish a blood vessel in the eye fundus.

2. Description of the Prior Art

In typical ophthalmological apparatuses such as optical coagulators or eye fundus blood velocimeters, a prescribed beam of monochromatic coherent light is projected to a region in the eye fundus and light scattered therefrom is detected to discriminate fundus blood vessels in order to recognize whether an eye being examined is moving or immobile There are also methods and apparatuses for obtaining color images of the eye fundus by scanning the eye fundus with light which includes the wavelength regions of the three primary colors, red (R), green (G) and blue (B), and discriminating fundus blood vessels by receiving the light thereby scattered by the eye fundus.

A drawback of systems based on the use of monochromatic light is that, during the examination procedure, any deviation in the alignment between the patient and the apparatus will change the quantity of scattered light that is detected, resulting in erroneous blood-vessel recognition. With apparatuses which project multichromatic light such as RGB light, for example, onto the eye fundus and detect and convert the scattered light from the eye fundus to obtain an image signal which is used to identify a blood vessel, attention must be paid to the fact that light absorbing and reflecting characteristics of the fundus blood vessels and surrounding tissues differ depending on the wavelength of the light concerned. This fact is not fully recognized in the prior art, so that the signal obtained from the scattered light has a poor signal-to-noise (S/N) ratio which gives rise to erroneous blood-vessel recognition.

SUMMARY OF THE INVENTION

An object of the present invention is therefore to provide a method and apparatus for discriminating eye fundus blood vessels which makes full use of differences in the light absorbing/reflecting characteristics in fundus blood vessels and surrounding tissues and is therefore able to reliably discriminate fundus blood vessels without error, even if there is a shift in the alignment between the apparatus and the eye.

In accordance with the present invention the above object is attained by a method and apparatus for discriminating eye fundus blood vessels. The method comprises the steps of projecting light having first and second wavelengths into the eye fundus, obtaining the difference, ratio, or the common logarithm of the ratio between the quantity of scattered light of the first and second wavelengths from the fundus blood vessel and surrounding tissue, and comparing the value thus obtained with a prescribed value.

The principle on which this arrangement is based, taking the example of red blood cells in a blood vessel of the eye fundus, is that blood cells, oxygenated or deoxygenated, have a higher reflectance to light with a wavelength in the range 600–660 nm than light with a wavelength in the 560–580 nm range, and a higher absorbance of light with a wavelength in the 560–580 nm range than light with a wavelength in the 600–660 nm range. While on the other hand, if the light is scattered by surrounding tissue, the above relationships will be reversed. Thus the present invention employs an arrangement comprising the steps of projecting light of two different wavelengths onto the eye fundus and detecting light scattered by blood vessels and surrounding tissue, converting this detected light into electrical signals and obtaining the difference, ratio, or the common logarithm of the ratio between the quantity of scattered light of the first and second wavelengths from the fundus blood vessel and surrounding tissue.

This invention fully utilizes the fact that light absorbing and light reflecting characteristics of fundus blood vessels and surrounding tissues depends on the wavelength of the light concerned, and, thus enables fundus blood vessels to be reliably discriminated.

BRIEF DESCRIPTION OF THE DRAWINGS

The purpose and features of the present invention will become more apparent from a consideration of the following detailed description taken in conjunction with the accompanying drawings in which.

DETAILED DESCRIPTION OF THE PREFERRED EMBODIMENT

Figure 1:
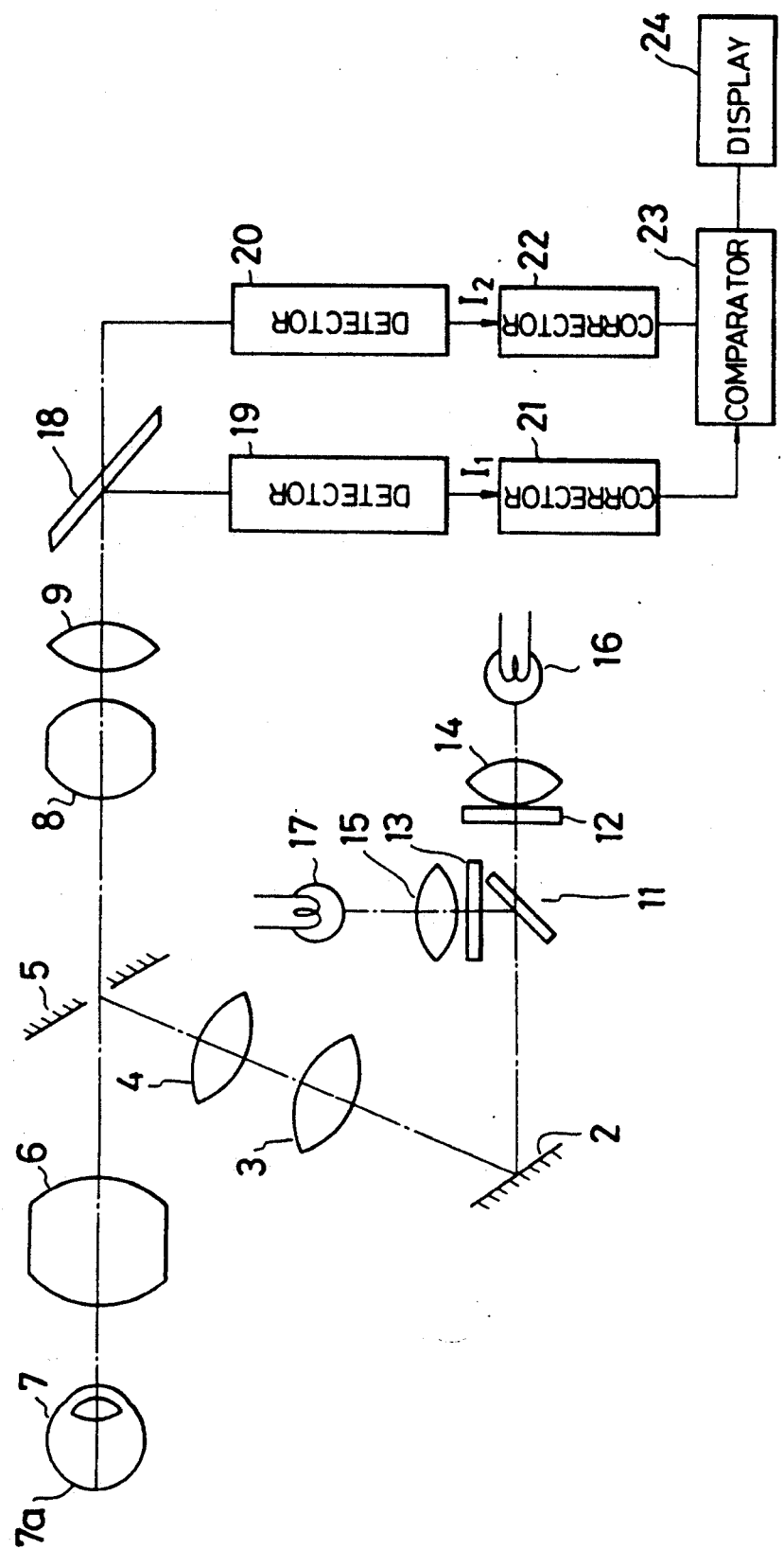
FIG. 1 is a drawing showing the general arrangement of an apparatus according to one embodiment of the invention.

The invention is described in detail below on the basis of the preferred embodiments illustrated in the drawings.

Figure 2A:
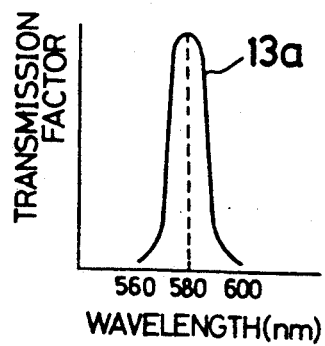
FIGS. 2a and 2b show characteristic curves of interference filters.
Figure 2B:
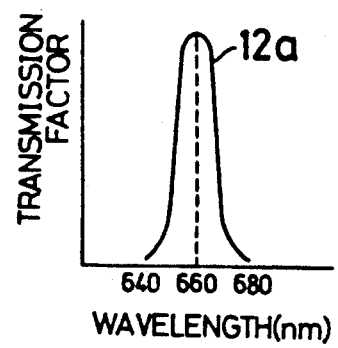
Figure 3:
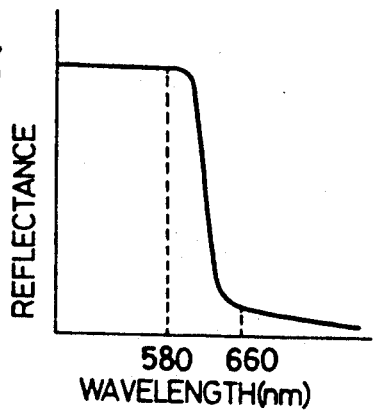
FIG. 3 shows a characteristic curve of a wavelength separation mirror.

With reference to FIG. 1 which shows the general arrangement of one embodiment of the apparatus of the invention, light from light sources 16 and 17 passes through condenser lenses 14 and 15 and interference filters 12 and 13 and is combined by a wavelength separation mirror 11. As illustrated by FIG. 2a, interference filter 13 has a peak at around 580 nm, while interference filter 12, as shown in FIG. 2b, has a peak at around 660 nm. The characteristics of the wavelength separation mirror 11 are shown in FIG. 3, showing that the reflectance of the mirror changes sharply in the 580–600 nm region. The wavelength separation mirror 11 combines light that passes through the interference filters 12 and 13, and therefore passes light with a 580 nm peak and light with a 660 nm peak.

The light is then reflected by a mirror 2 whereby it is directed through relay lenses 3 and 4 and is reflected by an annular mirror 5 and passes through an objective lens 6 and impinges onto a region in the fundus 7a of the subject's eye 7.

Scattered light from the eye fundus 7a passes back through the objective lens 6 and annular mirror 5, a focusing lens 8 and an image forming lens 9 and impinges on a wavelength separation mirror 18, which has the characteristics shown in FIG. 3. Light reflected by the wavelength separation mirror 18 will have a 580 nm peak, and this light is received by to a light intensity detector 19, comprising, for example, an imaging device. Light passed by the mirror 18 will have a 660 nm peak, and this light is likewise received by a light intensity detector 20, comprising, for example, an imaging device or the like.

Signals from the light intensity detectors 19 and 20 are input to correctors 21 and 22 and corrected, and are then compared by a signal comparator 23. A display 24 is used to show whether the light from the eye fundus was scattered by a blood vessel or scattered by surrounding tissue.

The operation of the apparatus thus arranged will now be described.

Figure 4A:
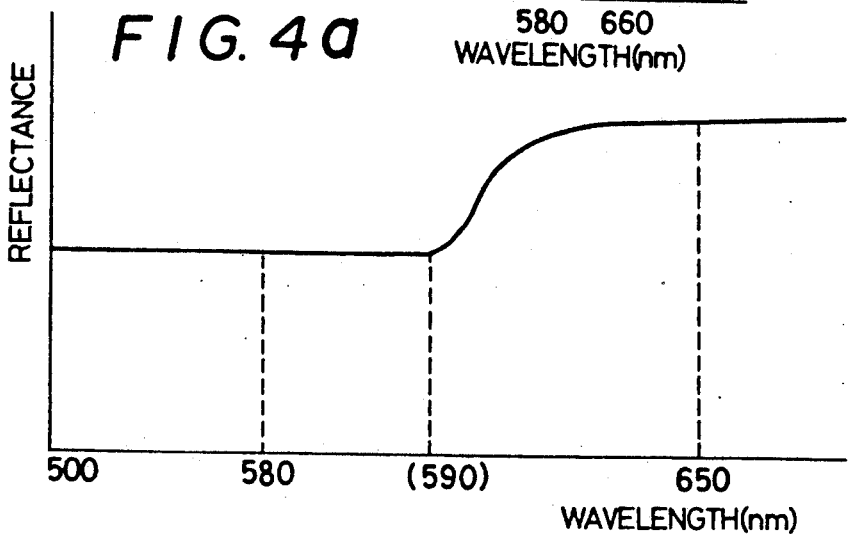
FIGS. 4a and 4b show the light reflecting and absorbing characteristics of blood vessel tissue.
Figure 4B:
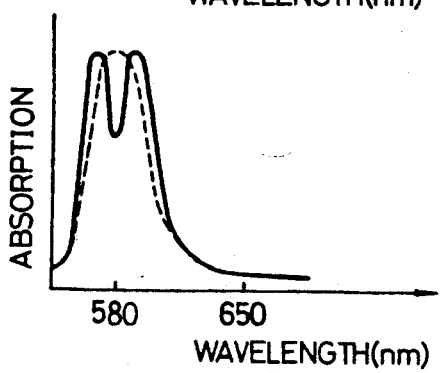
Figure 5A:
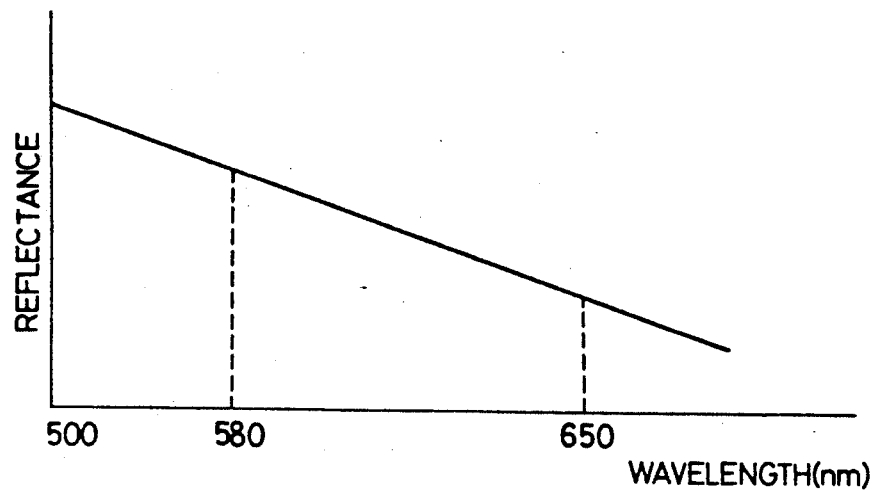
FIGS. 5a and 5b show the light reflecting and absorbing characteristics of surrounding tissue.
Figure 5B:
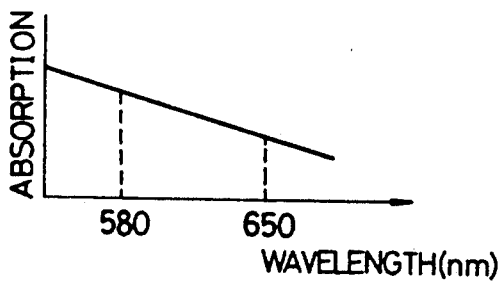

Red blood cells in a blood vessel of an eye fundus will normally have the type of reflectance characteristics shown in FIG. 4a, differing on each side of a 590 nm center. As shown in FIG. 4b, light absorption of both deoxygenated and oxygenated blood cells peaks at around 580 nm. The reflectance and absorption characteristics of the surrounding tissue are shown in FIGS. 5a and 5b, showing that as the wavelength of the light increases, there is a fall-off in both reflectance and absorption.

Therefore, blood cells, oxygenated or deoxygenated, in a blood vessel in the eye fundus will reflect more light with a wavelength in the 600-660 nm range than light with a wavelength in the 560-580 nm range, and will absorb more light with a wavelength in the 560-580 nm range than light with a wavelength in the 600-660 nm range. On the other hand, surrounding tissue will reflect more light with a wavelength in the 560-580 nm than light with a wavelength in the 600-660 nm range, and will absorb more light with a wavelength in the 600-660 nm range than light with a wavelength in the 560-580 nm range.

Therefore, if the intensity of scattered light with a wavelength in the 560-580 nm range is I1 and the intensity of scattered light with a wavelength in the 600-660 nm range is I2, in the case of a blood vessel $$I1 - \alpha I2 < 0 \qquad (1)$$

and in the case of surrounding tissue $$I1 - \alpha I2 > 0 \qquad (2)$$

Using a common logarithm to obtain the intensity ratio of the beams of scattered light gives $$\log(I1/\alpha I2) < 0 \qquad (3)$$

in the case of a blood vessel, and $$\log(I1/\alpha I2) > 0 \qquad (4)$$

in the case of surrounding tissue. Here, $\alpha$ is a correction coefficient, which will be described below.

Based on this principle, when scattered light from the eye fundus is divided by the wavelength separation mirror 18, scattered light with a wavelength of around 580 nm is input to the detector 19 and light with a wavelength of around 650 nm is input to the detector 20, whereby signals of intensities I1 and I2 are obtained from the respective detectors.

Because the amount of light with a wavelength in the 560-580 nm range will be different from the amount of light with a wavelength in the 600-660 nm range, and also because the detector sensitivity is wavelength dependent, the signal intensities detected by the detectors 19 and 20 in the case of an actual apparatus may not have the relationships illustrated by FIGS. 4a and b and 5a and b, so a correction coefficient $\alpha$ is applied to the signal level. For this, the signals from the detectors 19 and 20 are input to the correctors 21 and 22.

To effect blood vessel discrimination using the differences in the intensities of scattered light in the 560-580 nm and 600-680 nm range, a correction coefficient $\alpha$ must be selected that will ensure the equations (1) and (2) hold. For example, a correction coefficient could be used which would ensure that the signal level produced by the detector 19 which detects 580 nm light from blood vessel tissue is lower than that of the detector 20 which detects 650 nm light. This is determined by the ratio of light passed by the filters 12 and 13.

Signals from the correctors 21 and 22 are input into the signal comparator 23, where they are processed to extract the difference therebetween or the ratio of one to the other. To obtain the difference, the signals are binarized as plus or minus, i.e., in accordance with (1) or (2). To obtain the ratio, they are binarized as 1 or less or less than 1. On the basis of the binarized signals, the display 24 displays whether the illuminated region is a blood vessel or surrounding tissue.

When an imaging element is used as the detectors 19 and 20, the display 24 can display a digitized image of the blood vessel, and it is also possible for the diameter of the blood vessel to be displayed.

It goes without saying that if a scanning fundus camera is used to obtain image information from the intensities of the scattered light, the detectors 19 and 20 need not be imaging elements.

Figure 6:
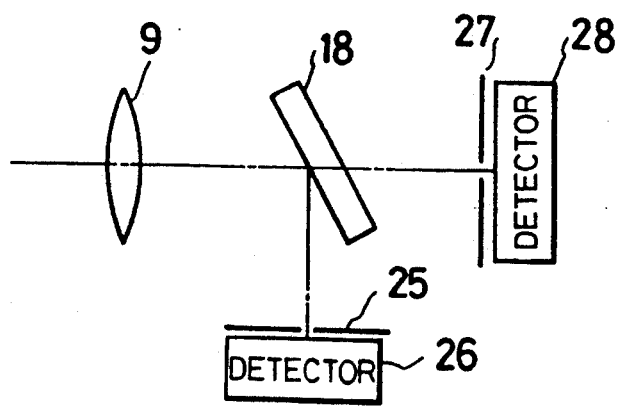
FIG. 6 is a drawing showing the arrangement of a detector which uses a photosensor device other than an imaging element.

Instead of an imaging element, an arrangement may be used such as the one shown in FIG. 6 in which a unit formed of a pinhole aperture 25 and detector 26 and a pinhole aperture 27 and detector 28 is positioned so that the pinhole apertures 25 and 27 are conjugate with the eye fundus. With this arrangement it becomes possible to determine whether the point on the eye fundus conjugate with the pinhole apertures 25 and 27 is or is not a blood vessel.

The embodiment described above shows the eye fundus blood vessel discrimination apparatus as modular, but it could be integrated into an actual ophthalmic apparatus with slight modifications without departing from the scope of the invention.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A method for discriminating eye fundus blood vessels in which a light beam of predetermined wavelength is projected into the eye fundus and light scattered therefrom is detected to distinguish blood vessels from surrounding tissue in the eye fundus, comprising the steps of:

projecting light of predetermined first and second wavelengths onto an eye fundus, the first wavelength light effective to better reflect from the surrounding tissue than the second wavelength light and the second wavelength light effective to better reflect from the blood vessels than the first wavelength light;

separately detecting first and second wavelength light scattered from fundus blood vessels and surrounding tissue;

obtaining the difference or the ratio, or the common logarithm of the ratio, between the detected light of the first and second wavelengths; and comparing the value thus obtained with a predetermined value to distinguish the blood vessels from surrounding tissue.

2. The method according to claim 1, wherein the scattered light is imaged and detected at an image plane that is conjugate with the eye fundus.

3. The method according to claim 1, wherein the projected light scans the eye fundus.

4. The method according to claim 1, wherein the first wavelength light has a predetermined wavelength selected from the range 560 nm to 580 nm and the second wavelength light has a predetermined wavelength selected from the range 600 nm to 660 nm.

5. A method for discriminating eye fundus blood vessels, comprising the steps of: projecting a first wavelength light and a second wavelength light onto an eye fundus; detecting the fist and second wavelength light scattered by the eye fundus blood vessels and surrounding tissue to produce a detected output; calculating from the detected output at least one of a difference, ratio or common logarithm of a ratio between the detected scattered first and second wavelength light to produce a corresponding calculated value; and comparing each corresponding calculated value with a respective predetermined value to discriminate the eye fundus blood vessels.

6. A method for discriminating eye fundus blood vessels according to claim 5; wherein the projected light scans the eye fundus.

7. A method for discriminating eye fundus blood vessels according to claim 5; wherein the scattered light is imaged and detected at an image plane that is conjugate with the eye fundus.

8. A method for discriminating eye fundus blood vessels according to claim 5; wherein the first wavelength light has a predetermined wavelength selected from the range 560 nm to 580 nm and the second wavelength light has a predetermined wavelength selected from the range 600 nm to 660 nm.

9. A method for discriminating eye fundus blood vessels according to claim 5; further comprising the step of correcting the detected output to maintain a detected relationship wherein the first wavelength light is detected as being better reflected from the surrounding tissue than the second wavelength light and the second wavelength light is detected as being better reflected from the blood vessels than the first wavelength light.

10. An apparatus for discriminating eye fundus blood vessels, comprising: projecting means for projecting a first wavelength light and a second wavelength light onto an eye fundus; detecting means for detecting the first and second wavelength light scattered by the eye fundus blood vessels and surrounding tissue to produce a detected output signal; calculating means for calculating from the detected output signal at least one of a difference, ratio or common logarithm of a ratio between the detected scattered first and second wavelength light to produce a corresponding calculated value; and comparing means for comparing each corresponding calculated value with a respective predetermined value to discriminate the eye fundus blood vessels.

11. An apparatus for discriminating eye fundus blood vessels according to claim 10; wherein the projecting means includes means for scanning the eye fundus.

12. An apparatus for discriminating eye fundus blood vessels according to claim 10; wherein the detecting means includes means for detecting and imaging the scattered light at an image plane that is conjugate with the eye fundus.

13. An apparatus for discriminating eye fundus blood vessels according to claim 10; wherein the first wavelength light has a predetermined wavelength selected from the range 560 nm to 580 nm and the second wavelength light has a predetermined wavelength selected from the range 600 nm to 660 nm.

14. An apparatus for discriminating eye fundus blood vessels according to claim 10; further comprising correcting means for correcting the detected output signal to maintain a detected relationship wherein the first wavelength light is detected as being better reflected from the surrounding tissue than the second wavelength light and the second wavelength light is detected as being better reflected from the blood vessels than the first wavelength light.

* * * * *